US00PP08903P

United States Patent [19]

Drewlow

[11] Patent Number: Plant 8,903

[45] Date of Patent: Sep. 20, 1994

[54] IMPATIENS PLANT NAMED AMBIENCE

[75] Inventor: Lyndon W. Drewlow, Ashtabula, Ohio

[73] Assignee: Mikkelsens, Inc., Ashtabula, Ohio

[21] Appl. No.: 165,590

[22] Filed: Dec. 13, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of Impatiens plant named Ambience, characterized by its red and pink bicolor flowers, relative large diameter flowers carried on light green pedicels, keel petals which are larger than its standard petals, solid deep green leaves, early flowering habit, highly self-branching and floriferous habits, flowering entirely above leaf canopy, tolerance to both high and cool temperatures, and its adaptability to be grown in 10 cm up to 15 to 25 cm containers.

1 Drawing Sheet

The present invention relates to a new and distinctive cultivar of Impatiens plant, botanically know as Impatiens, commercially known as New Guinea Impatiens, and known by its cultivar name Ambience.

The new cultivar was developed in a controlled breeding program conducted by the inventor Lyndon W. Drewlow in Ashtabula, Ohio. Ambience was created by crossing Mikkelsen Seedling No. 90-670-3 (seed parent) with Mikkelsen Seedling No. 90-658-1 (pollen parent). Both parents are proprietary cultivars used in the breeding program.

Asexual reproduction by terminal or stem cuttings carried out by or under the supervision of the inventor in Ashtabula, Ohio has shown that the unique features of Ambience are stabilized and are reproduced true to type in successive propagations.

The following combination of characteristics distinguish the new Impatiens from both its parent varieties and other cultivated Impatiens of this type known and used in the floriculture industry. In certain instances comparisons are made to the cultivars Sunburs (U.S. Plant Pat. No. 6,308) and Flambe.

1. Ambience has a red (45A to 45B) and pink (62B-C) bicolor flower which is deeper in color than the orange-red (34A) and almost white bicolor flowers of Sunburst but not as deep as the red (44A) and almost white bicolor flowers of Flambe.

2. Ambience has a larger diameter flower (6.0 to 6.5 cm) than Flambe (5.5 cm to 6.0 cm) and Sunburst (4.5 to 5.0 cm).

3. Flower pedicels of Ambience are light green and similar to Sunburst, while Flambe has pedicels which are reddish purple in color.

4. Ambience has larger keel petals than standard petals while both Sunburst and Flambe have similar sized keel and standard petals.

5. The flower spur on Ambience is 4.0 to 4.5 cm long and yellow green in color with a reddish blush which is a deeper blush than the 3.0 cm long flower spur on Sunburst. Flambe has a 4.0 to 4.5 cm long reddish-purple spur. All of these cultivars have a deep green tip on the flower spur.

6. Ambience has solid deep green leaves while Sunburst has deep green leaves with a trace of cream variegation at the basal end of the leaf around midrib under high light conditions. Flambe has deep green leaves with heavy cream variegation around the midrib.

7. Ambience has green stems with red tint while Sunburst has a deeper red cast to stems and Flambe has deep reddish purple stems.

8. Ambience is 7 to 10 days earlier to bloom than Sunburst and 4 to 7 days earlier than Flambe.

9. Ambience and Sunburst usually have two flowers per leaf axil while Flambe has only one.

10. The upper leaf surface of both Ambience and Sunburst is glabrous while the same surface of Flambe is glandular.

The accompanying color photograph comprises a top perspective view showing the overall appearance of Ambience, with the colors being as true as it is reasonably possible to obtain in a color reproduction of this type. The photograph was taken in Ashtabula, Ohio on Sep. 24, 1993 under natural light in a shaded glass greenhouse under 40% saran on a sunny day.

The following is a detailed description of Ambience, based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°-68° F. night temperatures under 3000–4000 foot candles of light and with 250 ppm nitrogen, 75 ppm potassium, and 250 ppm phosphorous nutritional levels, with trace elements added. Habit of growth, foliage coloration, leaf variegation, size of leaves and flower size will be influenced by nutritional and environmental conditions, without, however any variance in the genotype.

Color references are made to The Royal Horticultural Society Colour Chart except where general terms of ordinary dictionary significance are used.

Parentage: A controlled cross between female parent Mikkelsen Seedling No. 90-670-3 and male parent Mikkelsen Seedling No. 90-658-1.

Propagation:

A. *Type cutting.*—Stem tip 15 mm long will develop to 4 to 5 cm in length in 18 to 21 days.

B. *Time to root.*—8–10 days at 23° C. summer; 10–12 days at 20° C. winter.

C. *Rooting habit.*—Heavy, fibrous.

Plant description:

A. *Form and habit of growth.*—Mounded; semi-tall in height; flowers over the top of leaf canopy;

highly self-branched; continuous flowering; vigorous growing flowering herb.

B. Foliage.—Dark green leaves with reddish-purple cast to midrib. No leaf variegation; underside of leaf has reddish-purple cast, with midrib major veins the darkest. (1) Size: 11.0 to 12.0 cm long and 3.0 to 3.5 cm wide on average mature leaf. (2) Shape: Lanceolate with acuminate apex and acute base. (3) Texture: Both upper and lower surfaces are glabrous and somewhat rugose. (4) Margin: Entire with fine ciliate. (5) Color; Young foliage, top side between 146A and 147A, under side 183A; mature foliage, top side 147A, under side 183B. (6) Veination: Pinnate, green in color on upper leaf surface; reddish purple on lower leaf surface.

Flowering description:

a. *Flowering habits.*—Flowers continuosuly from leaf whorl of 6 to 7 leaves in progressively orderly manner with usually two flowers per leaf axil. However, some may have only one per leaf axil. All first flowers in a whorl open before the second flower in the leaf axis of that whorl starts to open. When the second flower in a leaf axil opens, the first flower in the leaf whorl above starts to open. It takes 5 to 7 days for a mature bud to open fully and them may last two weeks or longer depending on the environment.

B. *Natural flowering season.*—Indeterminate and continuous. Quantity of flowering increases with increases in light levels.

C. Flower buds.—Ellipsoidal, flowers perfect; yellow-green spur with slight reddish blush near sepal 4.0 to 4.5 cm long on mature bud with darker green tip; throat behind ovary and originating from major sepal.

D. *Flowers borne.*—On individual 4.0 c.m. long green pedicels from a whorl of usually 6 to 7 leaves. Flowering is progressive around the whorl as buds and leaves develop. Leaf axils usually have two flowers.

E. *Quantity of flowers.*—Numerous because of highly self-branched nature; two flowers per leaf axil; flowers are long lasting.

F. *Diameter of flowers.*—6.0 to 6.5 c.m.

G. *Petals.*—(1) Shape: Heart, with two keel petals being largest. (2) Color: Top side in summer when opening 45A to 45B and 62B to 62C bicolor, fading to 45C and 62D bicolor; under side 47D. (3) Number of petals; Five (5) (4) Size of petals: Standard: 2.5 cm long by 3.5 cm wide; two equal lobes, shallow cut. Wings: 3.0 cm long by 3.0 cm wide; two unequal lobes; shallow cut. Keel: 3.0 long by 3.5 cm wide; two unequal lobes; moderate cut.

H. *Reproductive organs.*—(1) Stamens: Number: Five (5). (a) Anther: Hooded shape; color is white with reddish cast. (b) Pollen color: Cream. (2) Pistels: (a) Stigma shape: Five (5) segmented column; color, reddish purple. (b) Style color: Reddish purple. (c) Ovaries: Five (5) in number, size is 6 mm when mature, color is green with reddish-purple cast.

*Disease resistance.*—No significant disease and insect problems noted to date.

OTHER IMPORTANT CHARACTERISTICS

1. Ambience is mounted, dense growing cultivar with flowering above leaf canopy. The comparison cultivars Flambe and Sunburst are more open growing plants with a portion of the flowers inside the leaf canopy.
2. The growing season outdoors of Ambience can be expanded since Ambience has shown the ability to continue to bloom under both high temperatures and sunlight, and will continue to bloom as well under cool temperatures (40°-50° F.).
3. Self-branching, early flowering habit allows Ambience to be grown in 10 cm pots, but its vigorous habit is such that it can be grown in 15 to 25 cm containers as well.

I claim:

1. A new and distinct cultivar of Impatiens plant named Ambience, as illustrated and described.

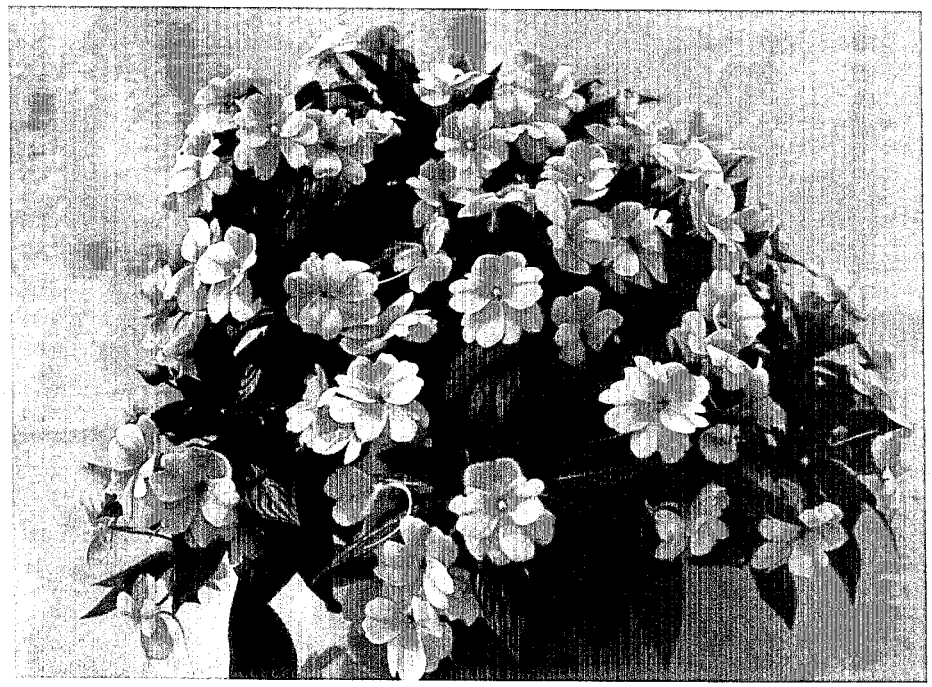

* * * * *